March 5, 1940. P. DOT Plant Pat. 366
ROSE PLANT
Filed July 13, 1939
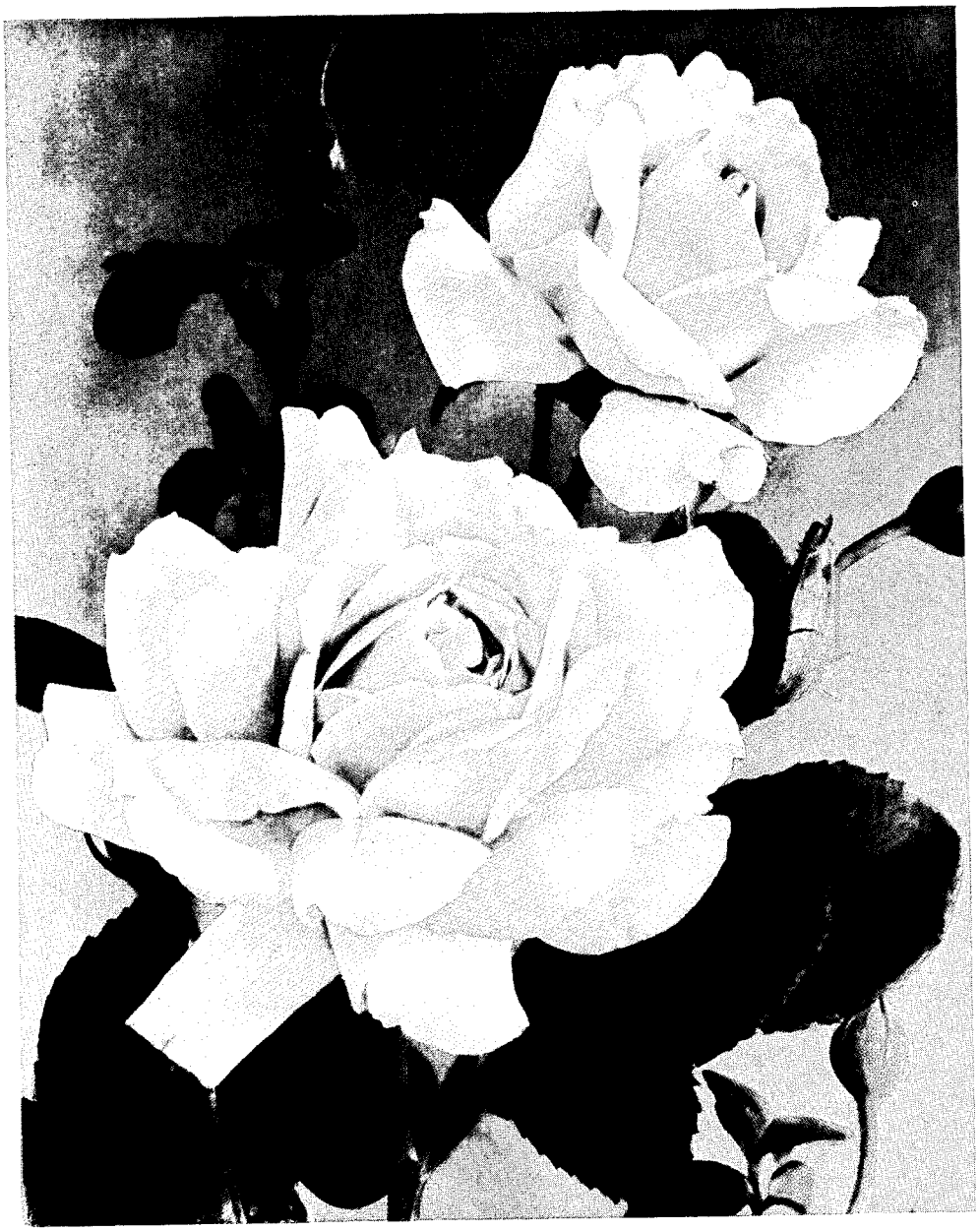
Inventor:
Pedro Dot
By Robbins & Robb
Attorneys Patented Mar. 5, 1940

Plant Pat. 366

UNITED STATES PATENT OFFICE

366

ROSE PLANT

Pedro Dot, Barcelona, Spain, assignor to The Conard-Pyle Company, West Grove, Pa.

Application July 13, 1939, Serial No. 284,363

1 Claim. (Cl. 47—61)

The present invention relates to a new and distinct Pernetiana rose plant, the result of a definite effort to produce a rose combining the fine qualities of both parents.

This new rose was produced by crossing Luis Brinas and Condesa de Sastago, the latter being particularly distinguished for its vigor of growth, freedom of bloom, size and quality of flower, and persistence of petalage. The result of this combination is a remarkable rose of a completely new and attractive coloring.

Other features of novelty and distinction are referred to in the following detailed description of the new variety, the color terminology being in accord with dictionary definitions, except where otherwise indicated:

Parentage:

*Seed parent.*—Luis Brinas.

*Pollen parent.*—Condesa de Sastago.

Classification.—Pernetiana.

Type.—Hardy; tall, outdoors; seedling; for cut flowers and garden decoration.

Propagation.—It holds its distinguishing characteristics through succeeding propagations by cuttings, grafting, budding and layering.

*Flower*

Locality where grown.—West Grove, Pennsylvania.

Flowers borne.—Single, several to stem; in irregular arrangement on normal medium length stems.

Quality of bloom.—Free outdoors.

Continuity.—Continuous.

Fragrance.—Moderate; Tea.

Bud:

*Peduncle.*—Medium length; medium bending; green; almost smooth; few red-green prickles.

*Before calyx breaks.*—Medium size.

*Form.*—Short, globular; with slender, much-cut foliaceous parts extending beyond the tip of the bud equal to ¾ or more of its length.

*As first petal opens.*—Medium size.

*Form.*—Pointed.

*Color.*—(Ridgway's.) Outside.—Light Salmon-Orange, Plate 2, with Lemon-Yellow base, Plate 4. Inside.—A blush of Orange-Pink, Plate 2, with Picric-Yellow base, Plate 2.

*Opening.*—Opens up well.

Bloom:

*Size, when fully open.*—Medium, 3 inches to 3½ inches.

*Petalage.*—Double; from 35 to 55 petals, arranged regularly.

*Form.*—Very globular at first, becoming cupped; petals remaining at first very cupped, becoming later at maturity very loosely rolled outward.

Petals.—Thick, leathery with inside and outside satiny.

*Shape.*—Oval. Intermediate.—Oval, scalloped with one notch. Inside.—Round

This description of a newly opened flower was made from a rose grown outdoors, September, 1938, at West Grove, Pennsylvania.

*Color.*—(Ridgway's.) Outside petal. Outside surface.—Cream-Buff with rosy-blush, Plate 30, with Strontian-Yellow base, Plate 16. Inside surface.—Cream-Buff, Plate 30, with Strontian-Yellow base, Plate 16. Inner petal. Outside surface.—Orient-Pink, Plate 2. Inside surface.—Orange-Pink, Plate 3.

This description was made from a rose that was open for three days outdoors, in September, 1938, at West Grove, Pennsylvania.

*Color.*—(Ridgway's.) Outside petal. Outside surface.—Maize Yellow to Buff Yellow with Lemon Yellow base, Plate 4. Outside petal. Inside surface.—Maize Yellow to Buff Yellow with Lemon-Yellow base, Plate 4. Inside petal. Outside surface.—Maize Yellow to Buff Yellow with Lemon-Yellow base, Plate 4 with blush flesh. Inside surface.—Maize Yellow to Buff Yellow with Lemon-Yellow base, Plate 4, with blush flesh.

*General color.*—(Ridgway's.) Newly opened flower.—Bittersweet Pink, Plate 2. Three days open.—Orange Buff to pale Orange Yellow, Plate 3.

*Behavior.*—Drop off cleanly.

*Flower longevity.*—On bush in garden, 4 to 5 days in September; cut roses grown outdoors kept at living room temperature 4 to 5 days in September.

Reproductive organs:

*Stamens.*—Medium number, arranged irregularly about pistils, tucked in calyx.

*Filaments.*—Medium length; Yellow; few with anthers.

*Anthers.*—Medium size; Yellow; open at various times.

*Pollen.*—Moderate; Gold.

*Pistils.*—Medium number.

*Styles.*—Uneven; medium size; medium heavy; bunched.

*Stigma.*—Yellow.

*Ovaries.*—Some protruding from calyx.
*Hips.*—None.
*Seeds.*—None.

*Plant*

Foliage:
*Leaves.*—Compound of 3–5; normal; medium size; leathery, glossy, wrinkled.
*Leaflets.*—Oval shape; with apex acute; base round; margin serrate.
*Color.* — Mature. Upper surface — Normal. Under surface—Light. Young. Upper surface — Moderately light. Under surface — Light.
*Rachis.*—(The supporting stem of the compound leaf) heavy. Upper side—Grooved, hairy. Under side—Sparsely prickly.
*Stipules.*—Long, medium width, with medium length points turning out at an angle of less than 45°.
*Disease.*—Subject to blackspot.

Growth:
*Habit.*—Upright, much branched.
*Growth.*—Vigorous.
*Canes.*—Medium heavy.
*Main stems.*—Green.
*Thorns.*—Several; long, hooked downward with long narrow base.
*Prickles.*—None.
*Hairs.*—None.
*Branches.*—Green.
*Thorns.*—Several; medium length, hooked downward with short narrow base.
*Prickles.*—None.
*Hairs.*—None.
*New Shoots.*—Bright Green.
*Thorns.*—Several; medium length, hooked downward with short narrow base.
*Prickles.*—None.
*Hairs.*—None.

I claim:

A new and distinct variety of rose plant of the Pernetiana class, characterized as to novelty by its vigor of growth, freedom of bloom, double petalage, and large size and attractive color combination of its flowers, substantially as shown and described.

PEDRO DOT.